(12) United States Patent
Ho et al.

(10) Patent No.: US 9,174,018 B2
(45) Date of Patent: Nov. 3, 2015

(54) EXHAUST VENT CONFIGURATION

(75) Inventors: Peter Chi Fai Ho, Pittsburgh, PA (US); Elizabeth Powell Margaria, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 853 days.

(21) Appl. No.: 13/131,616

(22) PCT Filed: Nov. 21, 2009

(86) PCT No.: PCT/IB2009/055249
§ 371 (c)(1),
(2), (4) Date: May 27, 2011

(87) PCT Pub. No.: WO2010/067237
PCT Pub. Date: Jun. 17, 2010

(65) Prior Publication Data
US 2011/0240030 A1 Oct. 6, 2011

Related U.S. Application Data

(60) Provisional application No. 61/121,591, filed on Dec. 11, 2008.

(51) Int. Cl.
*A61M 16/20* (2006.01)
*A61M 16/06* (2006.01)
*A61M 16/08* (2006.01)

(52) U.S. Cl.
CPC .............. *A61M 16/208* (2013.01); *A61M 16/06* (2013.01); *A61M 16/20* (2013.01); *A61M 16/0816* (2013.01); *A61M 2205/42* (2013.01)

(58) Field of Classification Search
CPC . A61M 16/00; A61M 16/06; A61M 16/0605; A61M 16/0666; A61M 16/08; A61M 16/20; A61M 16/208; A61M 16/209; A61M 2016/0661
USPC ............ 128/206.21, 200.24, 204.18, 204.25, 128/205.24, 207.12
See application file for complete search history.

(56) References Cited

U.S. PATENT DOCUMENTS 5,690,096 A * 11/1997 Burch ...................... 128/204.18
8,028,698 B2 * 10/2011 Hodos et al. ............. 128/206.21
8,122,886 B2 * 2/2012 Kwok et al. ............. 128/206.21

(Continued)

FOREIGN PATENT DOCUMENTS

WO WO02051486 A1 7/2002
WO WO02096342 A2 12/2002

(Continued)

Primary Examiner — Justine Yu
Assistant Examiner — Colin W Stuart
(74) Attorney, Agent, or Firm — Michael W. Haas

(57) ABSTRACT

A respiratory interface device including a fluid coupling device having a main body and an exhalation plate having a plurality of vent holes, the exhalation plate being separate from and coupled to the main body. The present invention further relates to a fluid coupling device including an exhaust portion having a plurality of vent holes having a tapered shape. A set of the vent holes has an incident angle that radiates and originates from a common point. The present invention also relates to an exhalation mechanism including a plurality of vent holes defined by a continuous straight inner wall extending from an interior surface to an exterior surface wherein an exterior circumference of the vent hole is offset with respect to an interior circumference.

10 Claims, 9 Drawing Sheets

(56) References Cited

U.S. PATENT DOCUMENTS

| | | |
|---|---|---|
| 8,205,615 B1 * | 6/2012 | Ho .......................... 128/205.24 |
| 2007/0062536 A1 | 3/2007 | McAuley |
| 2007/0095350 A1 | 5/2007 | Darkin |
| 2008/0276937 A1 | 11/2008 | Davidson |
| 2009/0065729 A1 * | 3/2009 | Worboys et al. .............. 251/367 |

FOREIGN PATENT DOCUMENTS

| | | |
|---|---|---|
| WO | WO2005018523 A2 | 3/2005 |
| WO | WO2006122369 A1 | 11/2006 |
| WO | WO2007045008 A1 | 4/2007 |
| WO | WO2008058330 A1 | 5/2008 |
| WO | WO2009136333 A1 | 11/2009 |

* cited by examiner

EXHAUST VENT CONFIGURATION

CROSS-REFERENCE TO RELATED APPLICATIONS

This patent application claims the priority benefit under 35 U.S.C. §119(e) of U.S. Provisional Application No. 61/121,591 filed on Dec. 11, 2008, the contents of which are herein incorporated by reference.

BACKGROUND OF THE INVENTION

1. Field of the Invention

The present invention relates to respiratory interface devices for transporting a gas to and/or from an airway of a user, and, in particular, to a respiratory interface device, such as a mask, that includes a fluid coupling device having various improved exhaust venting mechanisms.

2. Description of the Related Art

A variety of respiratory masks are known which contact the areas of the nose and/or mouth of a human user. The uses for such masks include high altitude breathing (aviation applications), swimming, mining, fire fighting, and various medical diagnostic and therapeutic applications.

In many such applications, a gas is provided at a positive pressure within the mask for consumption by the user. The gas is typically supplied to the user through an air inlet, such as an opening, provided in the mask. In addition, in order to facilitate the delivery of the gas to the mask, a fluid coupling device, such as a swivel conduit, is normally coupled to the air inlet opening of the mask. Specifically, one end of the fluid coupling device is coupled to the inlet of the mask and another end of the fluid coupling device is coupled, perhaps through one or more additional conduits, to an external gas source, such as a blower of a ventilator or other suitable device.

Respiratory masks also often include a mechanism for purging carbon dioxide generated by the user from the mask to the atmosphere. In one known respiratory mask assembly, the venting mechanism is provided in the fluid coupling device (e.g., an elbow device) connected to the air inlet of the mask in the form of a number of vent holes provided directly in the fluid coupling device when it is manufactured, such as by a molding or an assembly process.

As will be appreciated, the particular manufacturing process that is employed places limits on how the vent holes can be formed. For example, in a molding process used to form an elbow device, the shape and particular configuration of the vent holes is limited by the mold. Specifically, due to one or more undercuts, typically included in the mold used to make the elbow device, it may be difficult and impractical to form vent holes in the elbow device which taper from a large diameter on the interior of the elbow device to a smaller diameter on the exterior of the elbow device.

The present inventors recognized that there is room for improvement in the area of masks and similar respiratory interface devices, and, in particular, in the area of achieving a good venting mechanism for exhausting gases such as carbon dioxide generated by the user from the mask to the atmosphere.

SUMMARY OF THE INVENTION

In one embodiment, the invention provides a respiratory interface device including a first main body and a fluid coupling device. The fluid coupling device is operatively coupled to the first main body. The fluid coupling device has a second main body and an exhalation plate. The exhalation plate includes a plurality of vent holes. The exhalation plate is separate from and coupled to the second main body.

In one aspect, the invention provides an exhalation plate including an interior surface and an exterior surface, and each of the vent holes has an interior circumference at the interior surface and an exterior circumference at the exterior surface, and for each vent hole, the interior circumference is larger than the exterior circumference.

In another aspect, the invention provides that each of the vent holes has a tapered shape that tapers from an interior surface of the exhalation plate. In a further aspect, the tapered shape is a generally conical shape.

In another aspect, the invention provides an exhalation plate removably coupled to the second main body.

In another embodiment, the invention provides a fluid coupling device for a respiratory interface device. The fluid coupling device includes a main body and an exhaust portion. The exhaust portion has a plurality of vent holes having a tapered shape. A first set of the vent holes has an associated incident angle that radiates and originates from a common point.

In alternate aspects, the invention provides a first set of vent holes including all or only some of the plurality of vent holes.

In another aspect, the invention provides each of the first set of the plurality of vent holes has an associated incident angle that radiates and originates from a first common point, and each of a second set of the plurality of vent holes has an associated incident angle that radiates and originates from a second common point different than the first common point.

In a further embodiment, the invention provides an exhalation mechanism for a respiratory interface device including an interior surface, an exterior surface and a plurality of vent holes each extending from the interior surface to the exterior surface. The vent holes are defined by a continuous straight inner wall extending from the interior surface to the exterior surface. Each of the vent holes has an interior circumference at the interior surface and an exterior circumference at the exterior surface. For each vent hole, the exterior circumference thereof is offset with respect to the interior circumference thereof.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DESCRIPTION OF THE PREFERRED EMBODIMENTS

Figure 1:
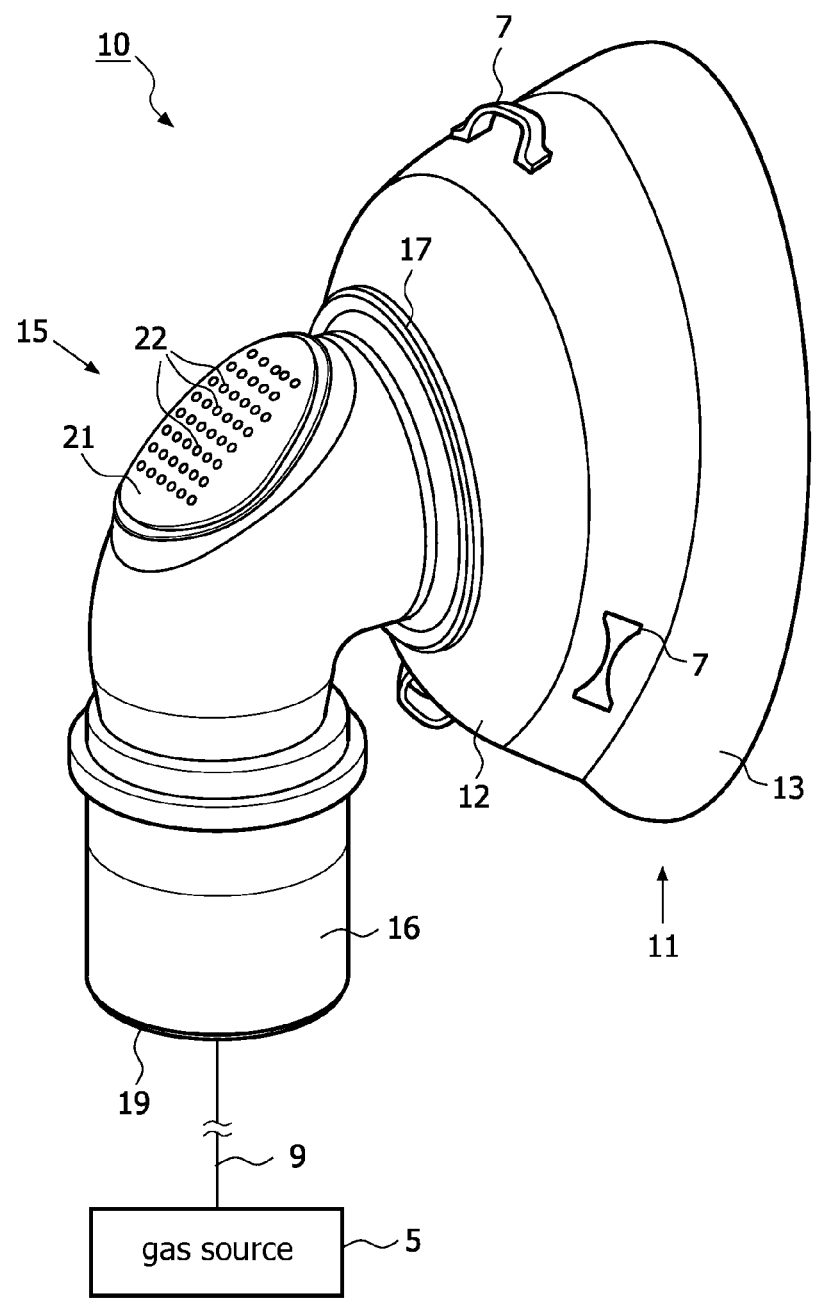
FIG. 1 is a partial, front isometric view of a respiratory mask according to an embodiment of the invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the term "interface device" refers to any suitable mechanism for transporting gas to and/or from the airway of a user and expressly includes, but is not limited to, non-invasive interface devices such as masks (e.g., without limitation, full face masks, nasal masks, and pillow masks having support elements such as forehead supports and cheek pads, including, without limitation, the Total™ face mask sold by the assignee hereof).

As employed herein, the statement that two or more parts or components are "coupled" or "connected" together shall mean that the parts are joined or operate together either directly or through one or more intermediate parts or components.

As employed herein, the term "number" shall mean one or an integer greater than one (i.e., a plurality).

FIG. 1 is a partial, front isometric view of a respiratory mask 10 according to an embodiment of the invention. As shown in FIG. 1, respiratory mask 10 includes a main body 11 having a faceplate 12. A fluid coupling device in the form of a swivel elbow 15 is coupled to faceplate 12. Swivel elbow 15 is for delivering a fluid, such as a breathing gas, from an external gas source 5, such as a blower or other suitable device, to the mask 10.

External gas source 5, which is also typically referred to as a pressure support system, is any conventional ventilation or pressure support system. Examples of such pressure support systems include, but are not limited to: a ventilator, continuous positive airway pressure (CPAP) device, or a variable pressure device, e.g. an auto-titrating device, proportional assist ventilation (PAV®) device, proportional positive airway pressure device, C-Flex™ device, Bi-Flex™ device, or a BiPAP® device manufactured and distributed by Philips Respironics, Inc. of Pittsburgh, Pa., in which the pressure provided to the patient varies with the patient's respiratory cycle so that a higher pressure is delivered during inspiration than during expiration, or other pressure support device. Other devices that communicate a flow of gas with an airway of a patient suitable for use in with the present invention include devices that apply a high and low or positive and negative pressure to the airway for purposes of secretion clearance of loosening.

Swivel elbow 15 has a main body 16 having a first elbow end 17 connected to the faceplate 12 of the mask 10 (received through an inlet (not shown) provided in the faceplate 12), and a second, opposite, elbow end 19 for connecting to an external gas source (not shown) through one or more additional conduits (not shown). First elbow end 17 can be threaded to provide for swivel movement with respect to the faceplate 12. Alternatively, first elbow end 17 may not be threaded and therefore not rotatably connected to the faceplate 12.

As shown in FIG. 1, second elbow end 19 is not threaded and therefore does not provide for swivel movement with respect to the external gas source or any conduits connected to the external gas source. Alternatively, second elbow end 19 can be threaded to provide for swivel movement with respect to the external gas source. Thus, in alternate embodiments, both first elbow end 17 and second elbow end 19 can be threaded to provide for swivel movement, or only second elbow end 19 can be threaded, or only first elbow end 17 can be threaded, or neither first elbow end 17 nor second elbow end 19 can be threaded in order to preclude swivel movement with respect to both faceplate 12 and the external gas source.

As shown in FIG. 1, an exhalation plate 21 is removably coupled to main body 16 of swivel elbow 15. Exhalation plate 21 includes a plurality of small vent holes 22, which can be arranged in a wide variety of diffusion patterns. In the exemplary embodiment shown in FIG. 1, vent holes 22 are arranged in a linear grid-like pattern. This, however, is meant to be exemplary only, and it will be understood that suitable patterns include any other configuration that allows the exhaust gas expired by the user to exit swivel elbow 15 through vent holes 22 to the atmosphere. Further, exhalation plate 21, as shown in FIG. 1, is in the shape of an elongated oval. This also is meant to be exemplary only, and suitable alternative shapes can include any shape that can be incorporated in swivel elbow 15.

Figure 2:
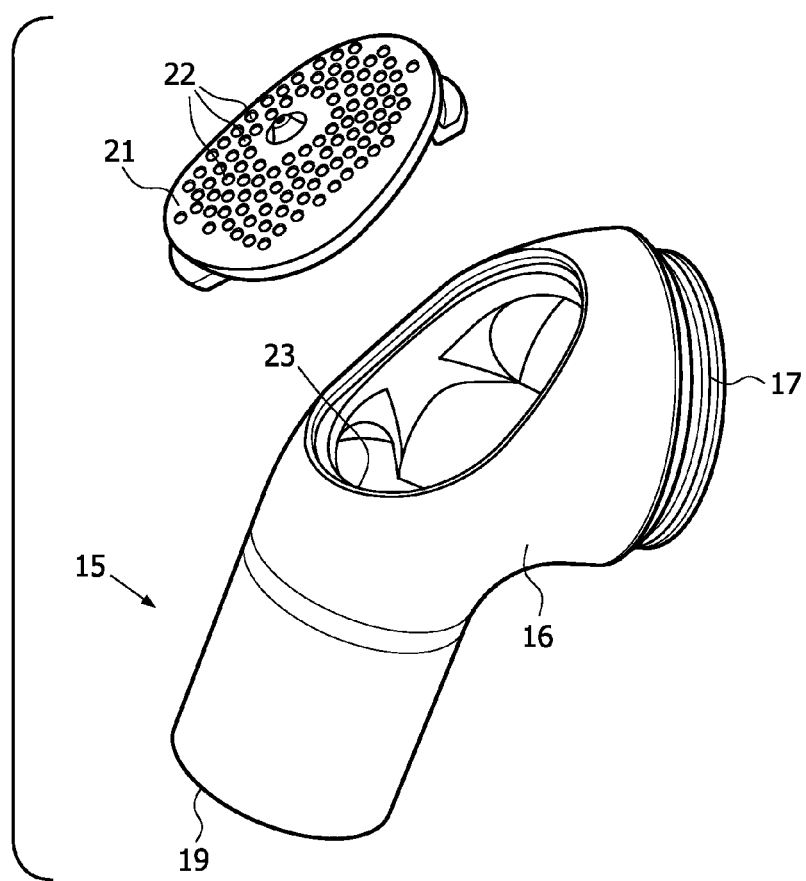
FIG. 2 is a front isometric view of the swivel elbow of FIG. 1 according to an embodiment of the invention.

FIG. 2 is a front isometric view of swivel elbow 15 of FIG. 1 showing exhalation plate 21 removed therefrom. As shown in FIG. 2, main body 16 of swivel elbow 15 defines an opening 23 to which exhalation plate 21 is removably attached. Exhalation plate 21 can be attached to swivel elbow 15 within opening 23 using a wide variety of attachment mechanisms known in the art, such as by mechanical snap fit (shown in FIG. 2), sonic welding, or gluing.

Because exhalation plate 21 is separate from the remainder of swivel elbow 15, it can be manufactured separately from the remainder of swivel elbow 15 and thus is not subject to limitations that may be imposed by the process used to manufacture the remainder of swivel elbow 15 such as, for example, limitations imposed by a molding process as described in the Background of the Invention section hereof. Such limitations may, for example, prevent the larger circumference of vent holes 22 from being located on the interior surface of swivel elbow 15. In addition, because exhalation plate 21 is removable, it can be readily replaced as needed, such as if it becomes damaged in some way.

Figure 3:
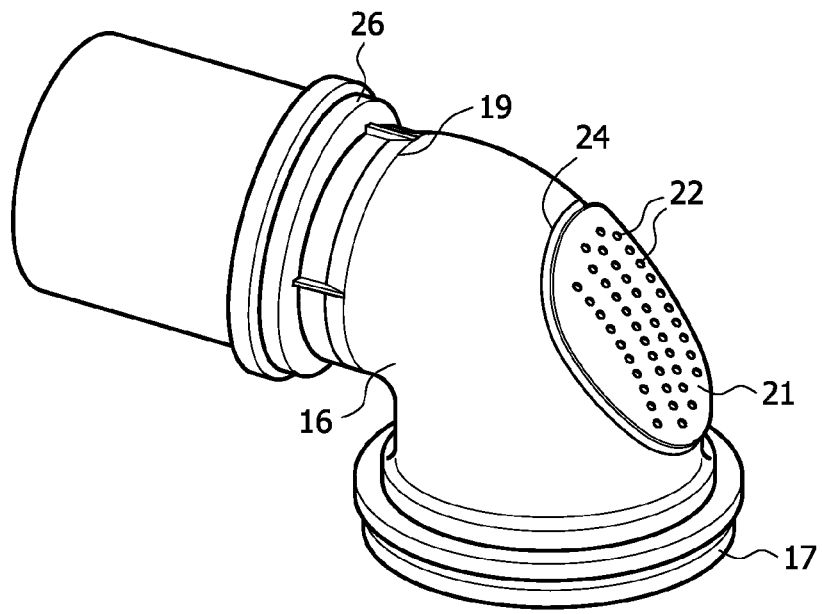
FIGS. 3 and 4 are front isometric views of a swivel elbow according to alternate embodiments of the invention.

FIG. 3 is a front isometric view of swivel elbow 24 according to an alternative embodiment of the invention. As seen in FIG. 3, swivel elbow 24 includes a number of the same components included as part of swivel elbow 15 shown in FIGS. 1 and 2, including a first elbow end 17 for connecting to a portion of a mask, such as faceplate 12 shown in FIG. 1 (not shown in FIG. 3), a second, opposite, elbow end 19, a removable exhalation plate 21 and vent holes 22. In addition, as shown in FIG. 3, a swivel conduit 26 is coupled to second elbow end 19. Swivel conduit 26 provides for swivel movement thereof relative to swivel elbow 24. Thus, as shown in FIG. 3, both first elbow end 17 and second elbow end 19 provide for swivel movement.

Figure 4:
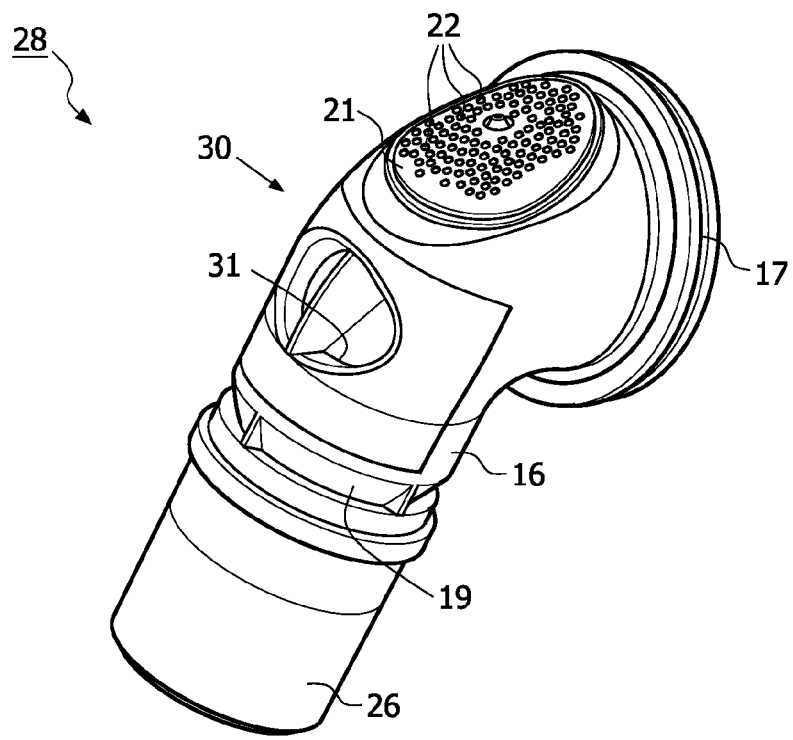
Figure 5:
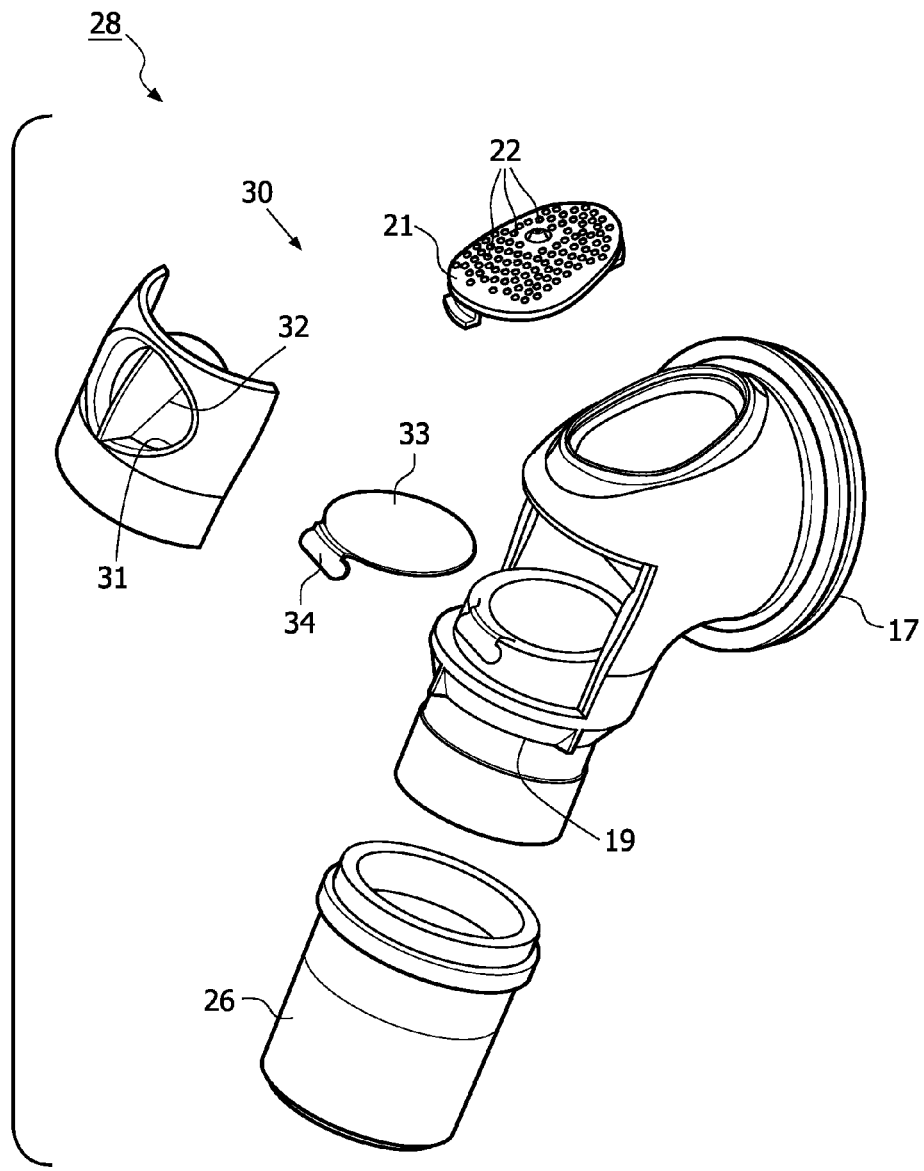
FIG. 5 is an exploded view of the swivel elbow of FIG. 4 according to an embodiment of the invention.
Figure 6:
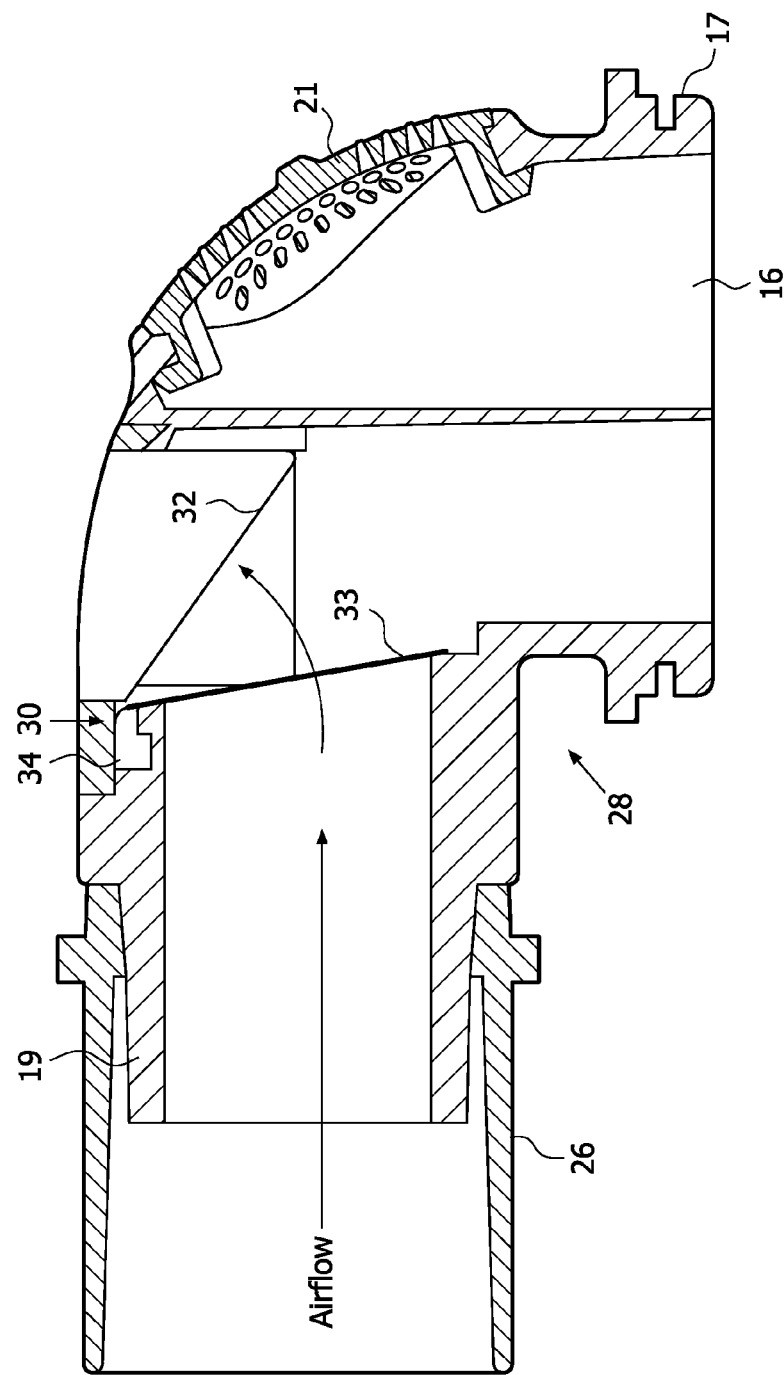
FIG. 6 is a cross-sectional view of the swivel elbow of FIG. 4 according to an embodiment of the invention.

FIG. 4 is a front isometric view, FIG. 5 is an exploded view and FIG. 6 is a cross-sectional view of swivel elbow 28 according to an another embodiment of the invention. As shown in FIG. 4, swivel elbow 28 includes a number of the same components included as part of swivel elbow 24 shown in FIG. 3, including a main body 16, a first elbow end 17, a second, opposite, elbow end 19, a swivel conduit 26, and a removable exhalation plate 21 having vent holes 22. In addition, as shown in FIGS. 4, 5 and 6, swivel elbow 28 includes an entrainment valve 30 providing for the inlet of air as needed, for example, in the case of an obstruction in the conduit that feeds the swivel elbow 28.

As shown in FIGS. 4, 5 and 6, entrainment valve 30 is positioned in the main body 16 of swivel elbow 28 between second elbow end 19 and exhalation plate 21. Entrainment valve 30 is separable from main body 16 and can be coupled to the main body 16 using a wide variety of fastening mechanisms known in the art, such as by mechanical snap fit, sonic welding, or gluing.

Referring to FIGS. 4, 5 and 6, entrainment valve 30 includes an aperture 31, a knife-edge seat 32, a disc 33 and a spring 34. If the pressure within the channel defined in the entrainment valve is equal to or less than ambient atmosphere, spring 34 will cause the disc 33 to shut off, thereby allowing air to flow through the aperture 31 of the entrainment valve 30. Spring 34 can be any suitable biasing mechanism, including, for example, a living hinge. Conversely a small positive pressure (during normal operation of the mask) causes disc 33 to lift, engage the knife-edge seat 32, and cover aperture 31 of entrainment valve 30, allowing air to flow freely through elbow 28 to mask 10.

Figure 7A:
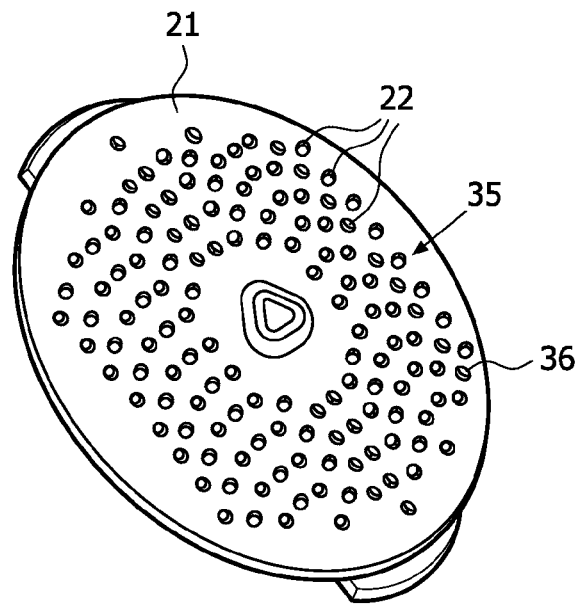
FIGS. 7A and 7B are front and rear isometric views, respectively, of an exhalation plate according to an embodiment of the invention.
Figure 7B:
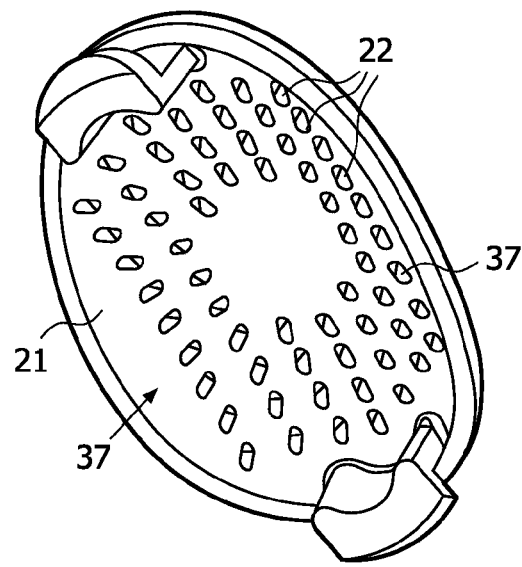

FIG. 7A is a front isometric view and FIG. 7B is a rear isometric view of exhalation plate 21 having venting holes 22 as shown in FIGS. 1, 2, 3, 4 and 5 according to one particular, non-limiting embodiment. FIG. 7A shows an exterior surface 35 of the exhalation plate 21, and FIG. 7B shows an interior surface 37 of exhalation plate 21. Also, FIG. 7A shows an exterior circumference 36 of vent holes 22. As used herein, the term "circumference" shall refer to a continuous perimeter having any shape, including, without limitation, circular, oblong, rectangular and triangular. FIG. 7B shows the interior circumference 37 of vent holes 22.

As seen by comparing FIG. 7A with FIG. 7B, exterior circumference (e.g., circular) 36 of vent holes 22 in the particular embodiment shown is smaller than interior circumference (e.g., oblong) 37 of vent holes 22. Thus, vent holes 22 in this embodiment have a tapered shape that tapers from interior circumference 37 to exterior circumference 36. In particular, vent holes 22 have a generally conical shape which tapers from an oblong shaped interior circumference 37 to a circular exterior circumference 36. Alternatively, vent holes 22 could have a true conical shape that tapers from a circular base, or any other suitable tapered shape that, for example, and without limitation, tapers from a square, rectangle or some other shaped base. As will be appreciated, creating an elbow by a molding process that includes such tapered vent holes (the larger area inside) directly in the elbow would require a complex mold. The need for such a complex mold is eliminated by using the separately formed exhalation plate 21.

FIGS. 7A and 7B are meant to be exemplary only, and it will be understood that in an alternative embodiment, vent holes 22 can have a tapered shape that tapers from exterior circumference 36 to the interior circumference 37. Thus, vent holes 22 can have a generally conical shape which tapers from an oblong or other shaped (e.g., rectangular, triangular) exterior circumference 36 to a smaller circular or other shaped (e.g., rectangular, triangular) interior circumference 37.

Figure 8:
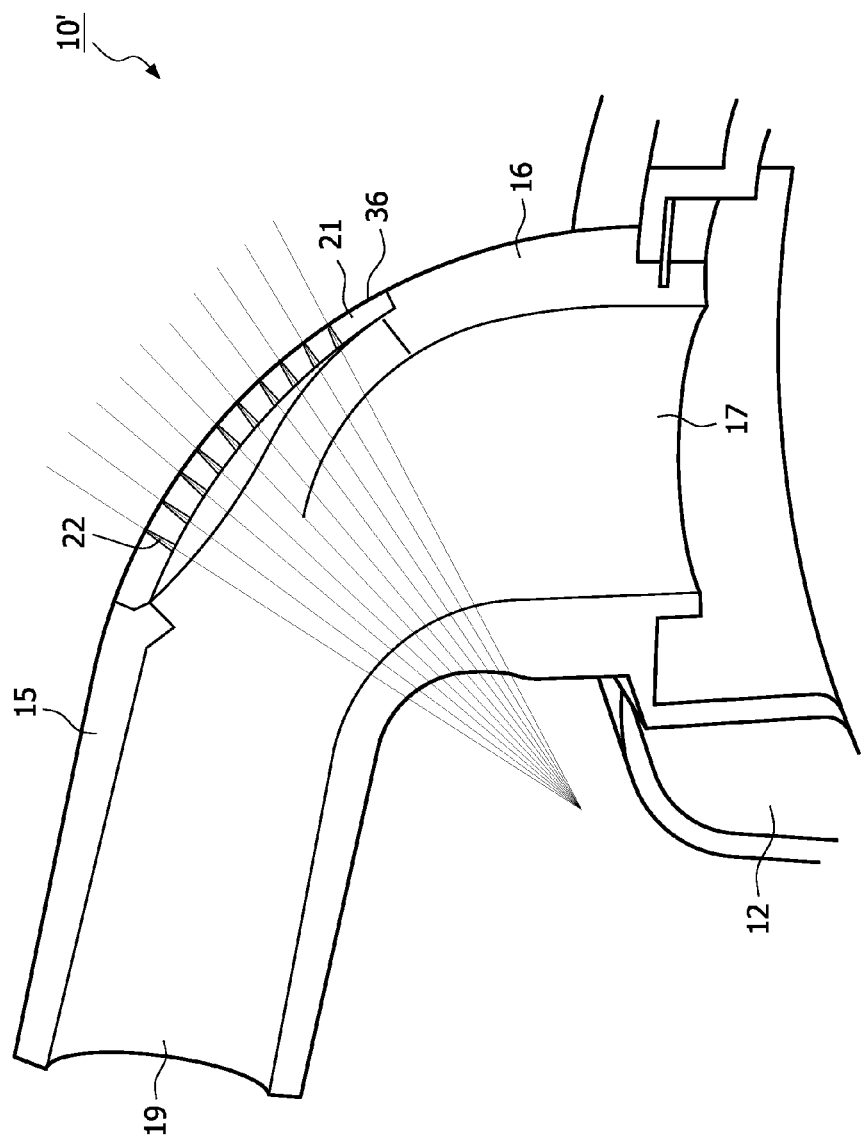
FIG. 8 is a partial side cross-sectional view of a respiratory mask according to an embodiment of the invention.

FIG. 8 is a partial side cross-sectional view of a respiratory mask 10' according to an embodiment of the invention that incorporates the particular embodiment of the exhalation plate 21 shown in FIGS. 7A and 7B. As seen in FIG. 8, the mask 10' includes a number of the same components included as part of the mask 10 in FIG. 1, including swivel elbow 15, a first elbow end 17 connected to faceplate 12, a second, opposite, elbow end 19, and exhalation plate 21 having vent holes 22 as just described. In addition, as shown in FIG. 8 and as just described, the vent holes 22 are generally conical in shape with the larger circumference being positioned on the interior surface 37 (shown in FIG. 7B) of the exhalation plate 21, and the smaller circumference being positioned on the exterior surface 36 of the exhalation plate 21. Preferably, the vent holes 22 have dimensions such that the ratio of the area of the larger circumference (e.g., oblong) to the area of the smaller circumference (e.g., circular) is greater than 1.

Further, the discharge of the exhaust flow from swivel elbow 15, 24, or 28, as the case may be, through vent holes 22 of exhalation plate 21 included therein, can be controlled and varied by altering the angles (i.e., degree of taper) of vent holes 22. For instance, each of vent holes 22 can be structured to have a different angle, or predetermined sets of vent holes 22 can each have a respective, common angle to form a specific pattern, or all of the vent holes 22 can have the same angle, as desired. Thus, the exhaust flow can be varied while the physical structure of swivel elbow 15, 24, or 28, and the exhalation plate 21 remain unchanged.

The particular embodiment of vent holes 22 shown in FIGS. 7A and 7B also provides for reducing the noise of the exhaust flow. In particular, a noise reduction can be achieved by discharging the exhaust flow through the tapered vent holes 22 wherein the vent holes 22 all have incident angles radiating from inside of the swivel elbow 15 as illustrated in FIG. 8 and originating from a common point. As shown in FIG. 8, each individual flow (ray) of exhaust exits out to the atmosphere at a unique angle such that the flows (rays) do not intersect. This eliminates resonance and reduces the noise level. Alternatively, multiple sets of vent holes 22 can have corresponding multiple common points of origin (see, for example, FIGS. 9A and 9B described in detail below, which show one particular embodiment).

Figure 9B:
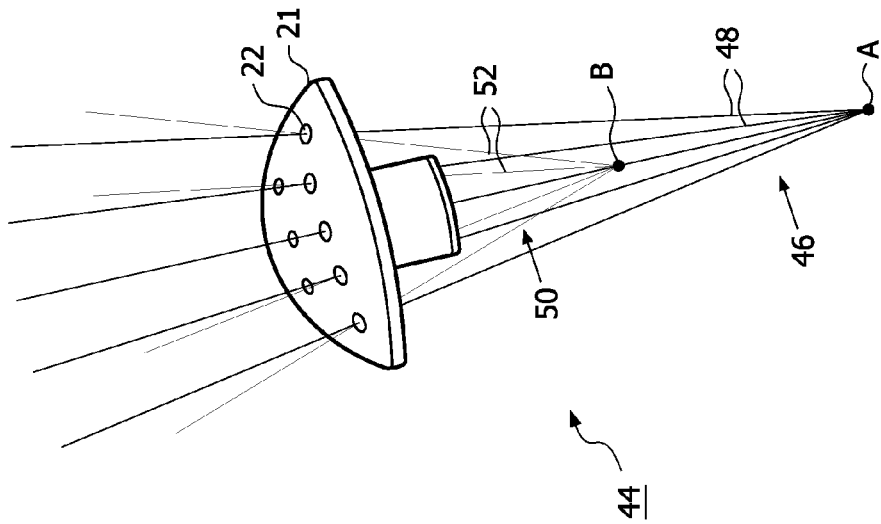
FIGS. 9A and 9B are side isometric views of vent holes in an exhalation plate according to an embodiment of the invention.
Figure 9A:
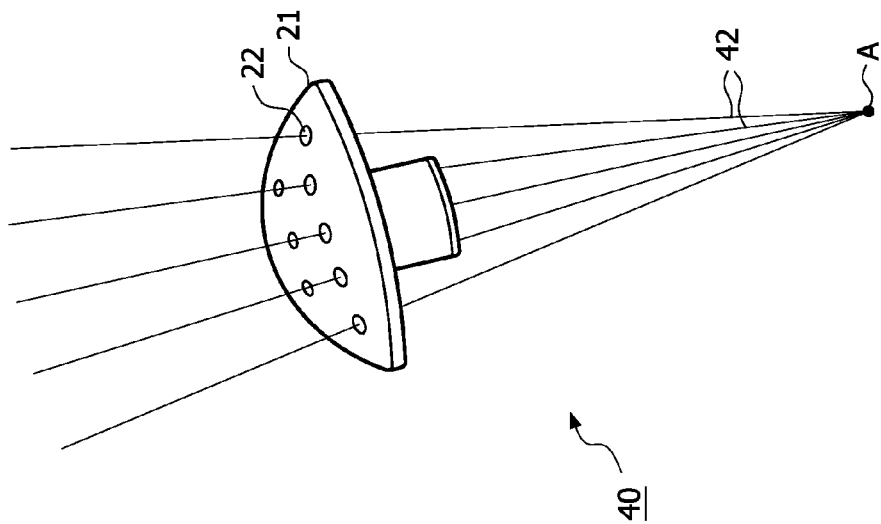

FIGS. 9A and 9B are side isometric views of the exhalation plate 21 and vent holes 22 according to particular, non-limiting embodiments. FIG. 9A shows an exhaust flow 40 comprising multiple rays 42 being discharged through each of the vent holes 22 having incident angles radiating from the inside of a swivel elbow (not shown) and originating from one common point A. Each of the individual rays 42 of exhaust flow 40 exits out each of an associated one of vent holes 22 to the atmosphere at a unique angle such that each of rays 42 does not intersect with one another.

FIG. 9B shows an exhaust flow 44 having a flow component 46 comprising multiple rays 48 and a flow component 50 comprising multiple rays 52. Rays 48 each exit out of an associated vent hole 22 and each have an incident angle that originates from a common point A. Similarly, rays 52 each exit out of an associated vent hole 22 and each have an incident angle that originates from a common point B. In the particular embodiment shown in FIG. 8B, the point of origin B is located approximately one-half as far from interior surface 37 as the point of origin A. It is contemplated that the set of vent holes 22 corresponding to the point of origin B have increased diffusion angles in comparison to the set of vent holes 22 corresponding to the point of origin A.

Figure 10A:
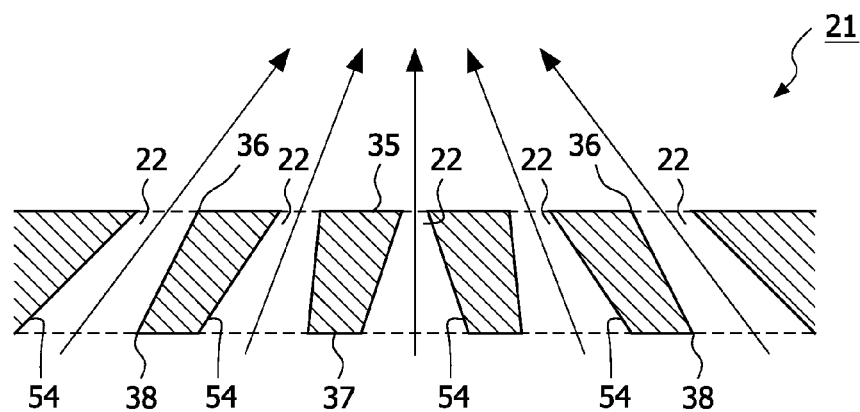
FIGS. 10A and 10B are schematic representations of vent holes in an exhalation plate according to alternate embodiments of the invention.

FIG. 10A is a schematic representation of a portion of exhalation plate 21 having vent holes 22 formed according to a particular preferred embodiment of the invention. As seen in FIG. 10A, each vent hole 22 is defined by a continuous, straight inner wall 54 formed within exhalation plate 21 extending from interior surface 37 to exterior surface 35. In other words, inner walls 54 do not curve or bend as they extend from the interior surface 37 to exterior surface 35.

Figure 10B:
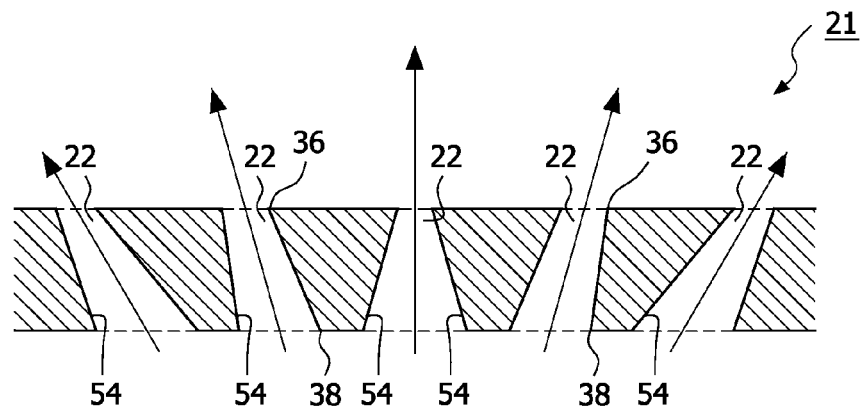

In the embodiment shown in FIG. 10A, the exterior circumference 36 of each vent hole 22 is smaller than interior circumference 38 of vent hole 22, the inner wall 54 is structured such that the exterior circumference 36 of vent hole 22 is offset (i.e., not centered within) with respect to the interior circumference 38 of vent hole 22. As seen in FIG. 10A, the particular offsetting results in convergent rays of flow. FIG. 10B is a schematic representation of an alternative embodiment of the exhalation plate 21 having continuous straight inner walls 54 wherein the offsetting of exterior circumference 36 with respect to interior circumference 38 of each vent hole 22 other than central vent hole 22 is such that divergent rays of flow are produced.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. For example, and without limitation, the exhalation plate 21 according to any of the particular embodiments described herein can be inserted directly into the faceplate of a mask rather than being inserted into a fluid coupling device coupled to the mask (as shown in FIG. 1). Accordingly, the invention is not to be considered as limited by the foregoing description but is only limited by the scope of the appended claims.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment

What is claimed is:

1. A respiratory interface device, comprising:
   a first main body; and
   a fluid coupling device operatively coupled to the first main body, the fluid coupling device including a second main body, and an exhalation plate, the exhalation plate comprising vent holes, the exhalation plate being separate from and coupled to the second main body, the vent holes have an arrangement selected from a plurality of linear rows and a non-linear pattern having a plurality of non-linear rows, wherein each vent hole in the arrangement has an associated incident angle, and wherein for all of the vent holes in the arrangement, each incident angle originates from a single common point.

2. The respiratory interface device according to claim 1, wherein the exhalation plate has an interior surface and an exterior surface, and wherein each of the vent holes has an interior circumference at the interior surface and an exterior circumference at the exterior surface, and wherein for each vent hole the interior circumference is larger than the exterior circumference.

3. The respiratory interface device according to claim 2, wherein for each vent hole a ratio of an area defined by the interior circumference to an area defined by the exterior circumference is greater than 1.

4. The respiratory interface device according to claim 1, wherein each of the vent holes has a tapered shape that tapers from an interior surface of the exhalation plate.

5. The respiratory interface device according to claim 4, wherein the tapered shape is a generally conical shape.

6. The respiratory interface device according to claim 1, wherein the fluid coupling device further comprises an entrainment valve, the entrainment valve being separate from and coupled to the second main body of the fluid coupling device.

7. The respiratory interface device according to claim 1, wherein the exhalation plate is removably coupled to the second main body.

8. The respiratory interface device according to claim 1, wherein during operation each vent hole has a ray of exhaust associated therewith, and wherein each ray of exhaust forms a unique angle such that the rays of exhaust do not intersect.

9. A fluid coupling device for a respiratory interface device, comprising:
   a main body; and
   an exhaust portion having vent holes having a tapered shape and the vent holes having an arrangement selected from a plurality of linear rows and a non-linear pattern having a plurality of non-linear rows, wherein each of the vent holes in the arrangement has an associated incident angle and wherein for all of the vent holes in the arrangement, each incident angle radiates and originates from a single common point.

10. An exhalation mechanism for a respiratory interface device, comprising:
    an interior surface;
    an exterior surface; and
    vent holes each extending from the interior surface to the exterior surface, the vent holes having an arrangement selected from a plurality of linear rows and a non-linear pattern having a plurality of non-linear rows, each of the vent holes being defined by a continuous straight inner wall extending from the interior surface to the exterior surface, each of the vent holes having an interior circumference at the interior surface and an exterior circumference at the exterior surface, wherein for each vent hole the exterior circumference thereof is offset with respect to the interior circumference thereof, and wherein each vent hole in the arrangement has an associated incident angle, and wherein for all of the vent holes in the arrangement, each incident angle originates from a single common point.

* * * * *